(12) United States Patent
Morimoto et al.

(10) Patent No.: US 6,271,615 B1
(45) Date of Patent: Aug. 7, 2001

(54) BRUSH HOLDER

(75) Inventors: Yoshihiro Morimoto; Shigeru Shiroyama, both of Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/355,629

(22) PCT Filed: May 26, 1997

(86) PCT No.: PCT/JP97/01768

§ 371 Date: Aug. 2, 1999

§ 102(e) Date: Aug. 2, 1999

(87) PCT Pub. No.: WO98/54821

PCT Pub. Date: Dec. 3, 1998

(51) Int. Cl.[7] .................................................. H02K 13/00
(52) U.S. Cl. ........................................... 310/239; 310/242
(58) Field of Search ..................................... 310/239, 242, 310/245, 91; 29/596–598

(56) References Cited

U.S. PATENT DOCUMENTS

| | | | |
|---|---|---|---|
| 5,148,072 | * | 9/1992 | Shiroyama ............................ 310/239 |
| 5,397,952 | * | 3/1995 | Decker et al. ....................... 310/242 |
| 5,939,812 | * | 8/1999 | Wetzel ................................. 310/245 |
| 6,005,323 | * | 12/1999 | Morimoto et al. .................... 310/239 |

FOREIGN PATENT DOCUMENTS

| | | |
|---|---|---|
| 58-70073 | 5/1983 | (JP) . |
| 62-95474 | 6/1987 | (JP) . |
| 3-18658 | 2/1991 | (JP) . |
| 6-74079 | 10/1994 | (JP) . |
| 5-60154 | 8/1996 | (JP) . |

* cited by examiner

*Primary Examiner*—Tran Nguyen
(74) *Attorney, Agent, or Firm*—Sughrue, Mion, Zinn, Macpeak & Seas, PLLC (57) ABSTRACT

The present invention provides a brush holder assembly structurally avoiding electrical short circuiting incidents involving positive-side leads, improving productivity and enabling costs to be reduced.

Tabs for securing positive-side brush holder frames are disposed in diagonally opposite positions. The tabs disposed on the side out of which the leads pass are positioned radially outside the range of movement of the positive-side leads and the tips of the tabs are bent in directions in which the positive-side leads do not come into contact therewith. On the other hand, the tips of the tabs disposed on the opposite side from the side out of which the leads pass are bent in the opposite direction to the tips disposed on the side out of which the leads pass.

3 Claims, 7 Drawing Sheets

BRUSH HOLDER

TECHNICAL FIELD

The present invention relates to improvements to a brush holder assembly for use in a direct-current electric motor.

BACKGROUND ART

An example of a conventional brush holder assembly for use in a direct-current electric motor is disclosed in Japanese Utility Model Laid-Open No. HEI 3-18658. The construction of the conventional brush holder assembly will be explained below with reference to FIGS. 7 to 11.

Figure 7:
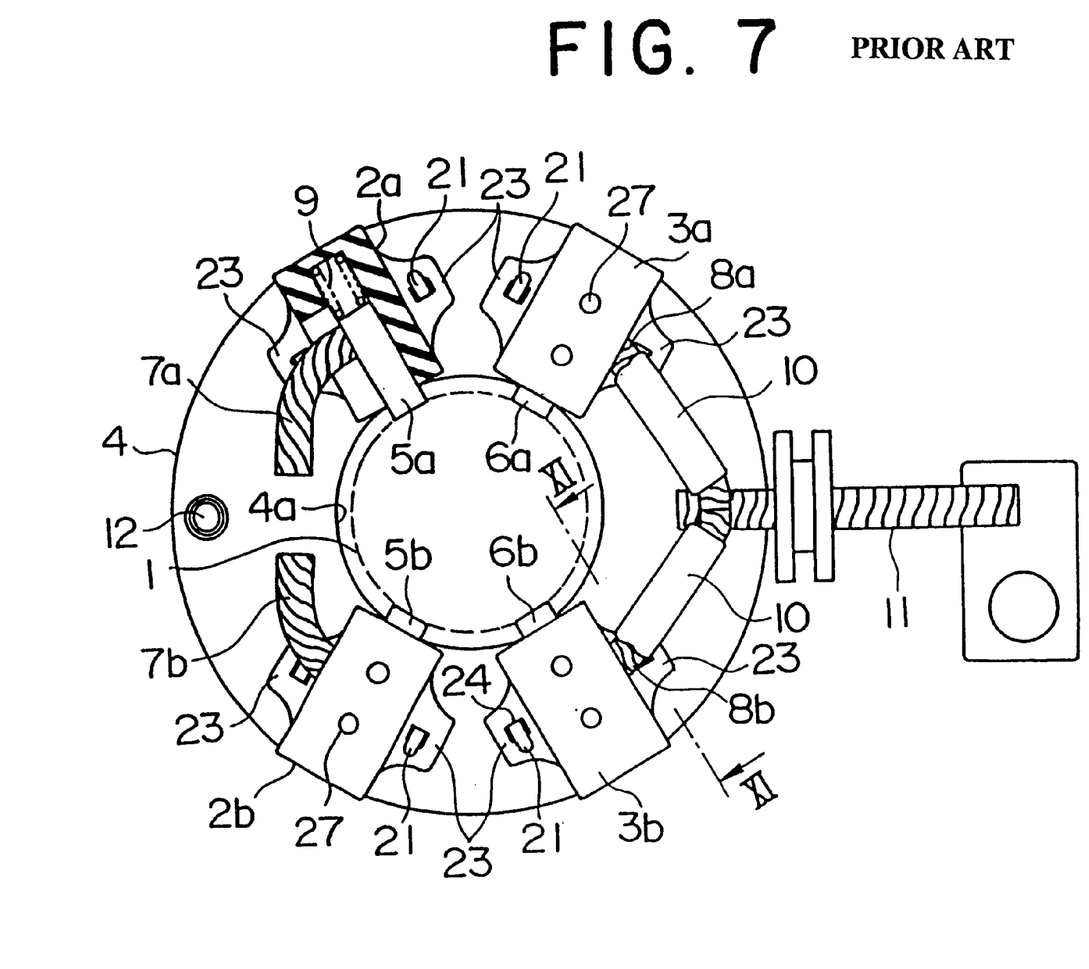
FIG. 7 is a plan of a conventional brush holder assembly.

The brush holder assembly comprises a pair of negative-side brush holder frames 2a, 2b and a pair of positive-side brush holder frames 3a, 3b fastened to a base 4.

The base 4 is a steel plate formed into an annulus having a central opening 4a being designed to allow passage of a commutator 1. A plurality of tabs 21 are disposed on the base 4 by press working part of the base 4.

Furthermore, the brush holder frames 2a, 2b, 3a, 3b are molded from electrically-insulating synthetic resin.

Figure 8:
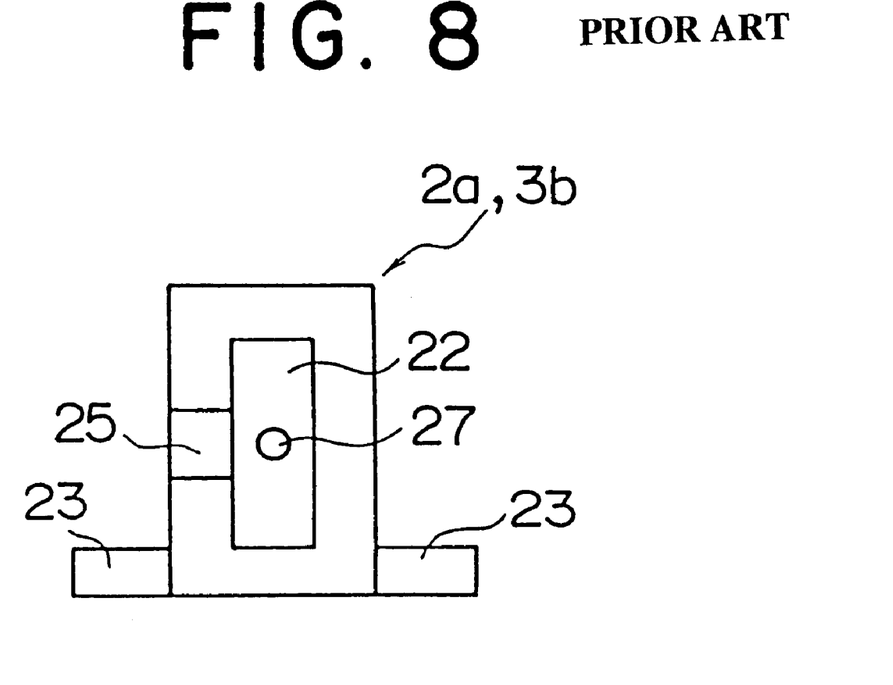
FIG. 8 is a front elevation of one of the brush holder frames applied to the conventional brush holder assembly.
Figure 9:
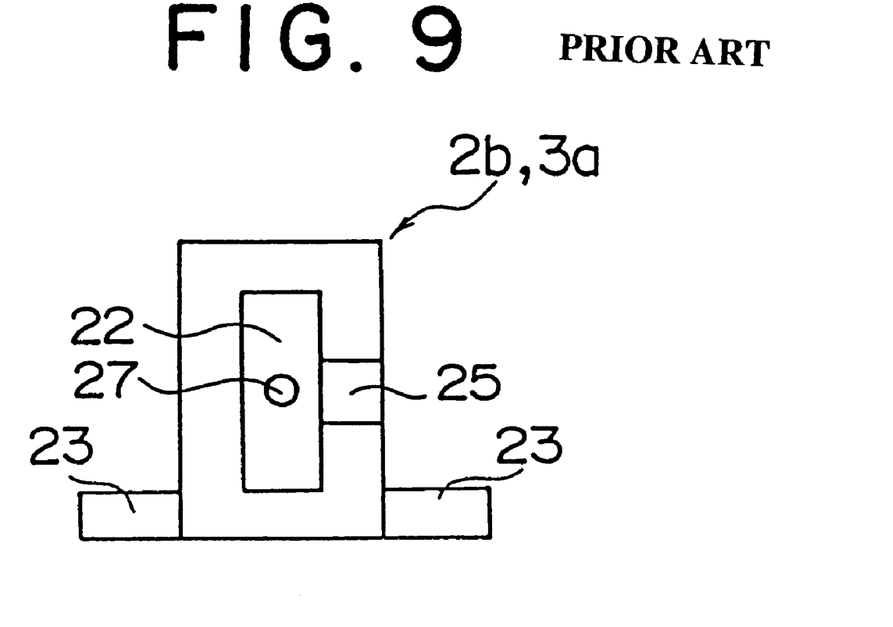
FIG. 9 is a front elevation of the other brush holder frame applied to the conventional brush holder assembly.

Brush receiving recesses 22 are disposed in brush holder frames 2a, 3b, respectively, so as to extend from a first end towards a second end without penetrating the second end. Furthermore, pairs of flanges 23 are disposed such that each extends outwards from a central portion of the bottom end on either side. Fastening slots 24 are disposed on each pair of flanges 23. Furthermore, a lead outlet groove 25 is disposed on one side so as to extend from the first end towards the second end and join the brush receiving recess 22 to the outside. Furthermore, a plurality of radiator openings 27 are provided.

On the other hand, brush holder frames 2b, 3a are constructed similarly to brush holder frames 2a, 3b above, except that the lead outlet groove 25 is disposed on the opposite side of each so as to extend from the first end towards the second end and join the brush receiving recess 22 to the outside.

Figure 10:
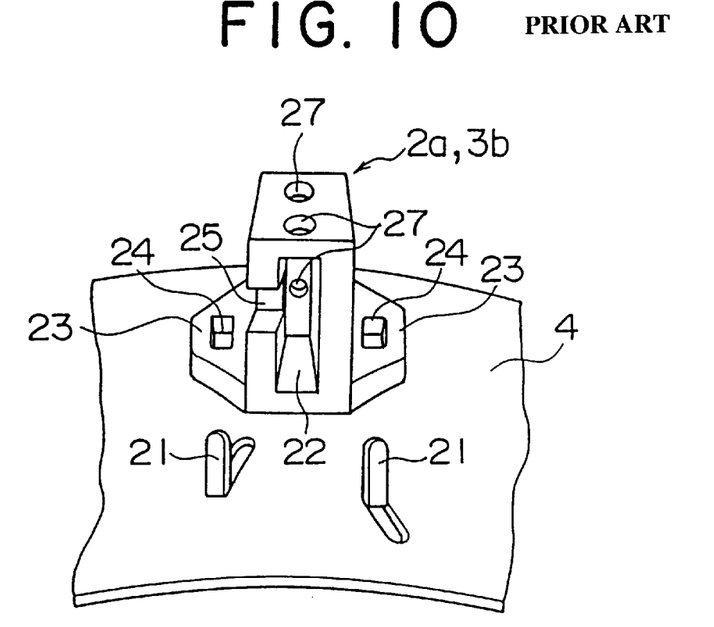
FIG. 10 is a partial perspective showing the method of mounting a brush holder frame in a conventional brush holder assembly.

The brush holder frames 2a, 2b, 3a, 3b are fastened onto the base 4 by passing the tabs 21 through the fastening slots 24 and bending the tips of the tabs 21 projecting from the fastening slots 24. At that point, the brush holder frames 2a, 2b, 3a, 3b are fastened to the base 4 such that the open ends of the brush receiving recesses 22 each face the central opening 4a of the base 4 and the axes of the brush receiving recesses 22 pass through the central axis of the central opening 4a of the base 4. The tabs 21 securing each of the brush holder frames are bent in mutually opposite radial directions, preventing the brush holder frames from dislodging in the axial direction.

Negative-side brushes 5a, 5b are inserted into the brush receiving recesses 22 of brush holder frames 2a, 2b, respectively, by passing negative-side leads 7a, 7b through the lead outlet grooves 25. Similarly, positive-side brushes 6a, 6b are inserted into the brush receiving recesses 22 of brush holder frames 3a, 3b, respectively, by passing positive-side leads 8a, 8b through the lead outlet grooves 25. The brushes 5a, 5b, 6a, 6b are placed in contact with the outer circumferential surface of the commutator 1 inserted through the central opening 4a of the base 4 by the force of brush springs 9 disposed within each of the brush receiving recesses 22.

The negative-side leads 7a, 7b connected to the negative-side brushes 5a, 5b and forming a pigtail are grounded by connection to the base by welding, etc. On the other hand, the positive-side leads 8a, 8b connected to the positive-side brushes 6a, 6b and forming a pigtail are connected to a power source (not shown) by means of a connector 11. The positive-side leads 8a, 8b are covered with insulating tubing 10 to prevent electrical short-circuiting with the base 4.

This brush holder assembly is mounted on an end bracket of direct-current electric motor using screw holes 12 disposed in the base 4.

Figure 11:
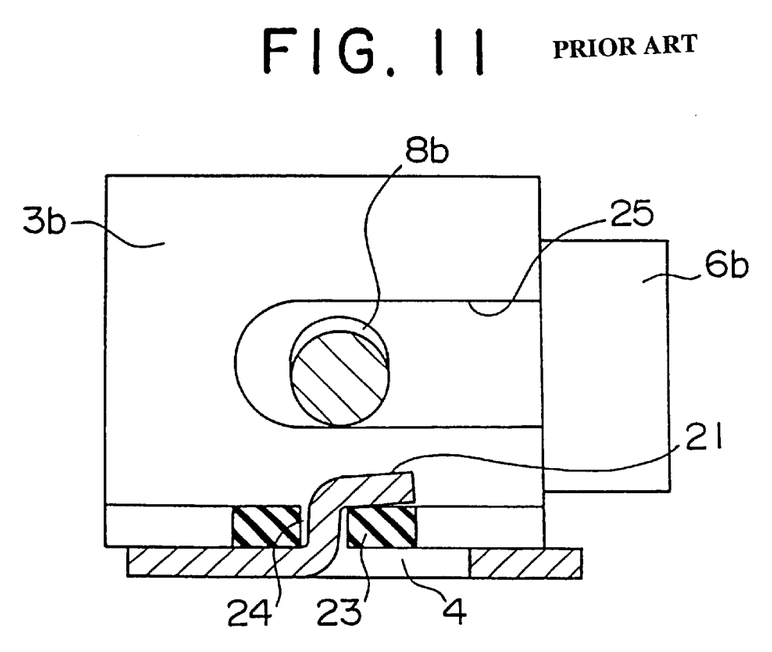
FIG. 11 is a cross-section taken along line XI—XI in FIG. 7 viewed from the direction of the arrow.

In a conventional brush holder assembly, the positive-side brush holder frames 3a, 3b are secured to the base 4 by passing tabs 21 disposed on the base 4 through the fastening slots 24 disposed in the flanges 23 extending outwards from central portions of the bottom end on either side thereof and bending the tips of the tabs 21 projecting from the fastening slots 24. Thus, as shown in FIG. 11, the tabs 21 and the leads 8a, 8b are in close proximity. Moreover, as the brushes 6a, 6b are worn down by the commutator 1, they are moved towards the commutator 1 by the force of the brush springs 9. With the movement of the brushes 6a, 6b towards the commutator 1, the leads 8a, 8b move within the outlet grooves 25 towards the commutator 1.

During operation of the direct-current electric motor, the leads 8a, 8b are on the positive electrode side, and the base 4, including the tabs 21, is on the negative electrode side. Thus, it has been necessary to cover the leads 8a, 8b with the insulating tubing 10 because there is a risk that the leads 8a, 8b and the tabs 21 will touch and short circuit electrically. For that reason, a problem has been that because of the necessity to have the tubing 10, an operation for covering the leads 8a, 8b with the tubing 10 has been required, making it difficult to reduce costs.

DISCLOSURE OF THE INVENTION

The present invention aims to solve the above problems and an object of the present invention is to provide a brush holder assembly not requiring tubing to cover the positive-side leads to prevent electrical short circuiting because electrical short circuiting incidents in the positive-side leads are prevented beforehand.

The brush holder assembly according to the present invention comprises:

a base made of steel plate having a passage for the insertion of a commutator and having a plurality of tabs for fastening disposed on a main surface thereof, a plurality of brush holder frames each made of insulating synthetic resin and comprising a brush receiving recess having an opening at a first end and a closure at a second end, a lead outlet groove disposed in one side so as to extend from the first end towards the second end and join the brush receiving recess to the outside, and flange portions each extending outwards from the bottom end on either side, the brush holder frames being disposed on the base such that the openings of the brush receiving recesses face the passage and the brush receiving recesses are directed towards the central axis of the passage, and being secured to the base by bending the tips of the tabs;

at least one positive-side brush inserted into the brush receiving recess and held by a brush holder frame by passing a positive-side lead attached to the side thereof through the lead outlet groove in the brush holder frame;

at least one negative-side brush inserted into the brush receiving recess and held by a brush holder frame by passing a negative-side lead attached to the side thereof out through the lead outlet groove in the brush holder frame; and a plurality of brush springs disposed within each of the brush receiving recesses of the brush holder frames for applying force to the positive-side and negative-side brushes in the direction of the central axis of the passage, wherein the tabs for securing the brush holder frames holding the positive-side brushes are disposed in-positions where the tabs will not contact the positive-side leads.

BEST MODE FOR CARRYING OUT THE INVENTION

The preferred embodiments of the present invention will be explained below with reference to the drawings.

Embodiment 1

Figure 1:
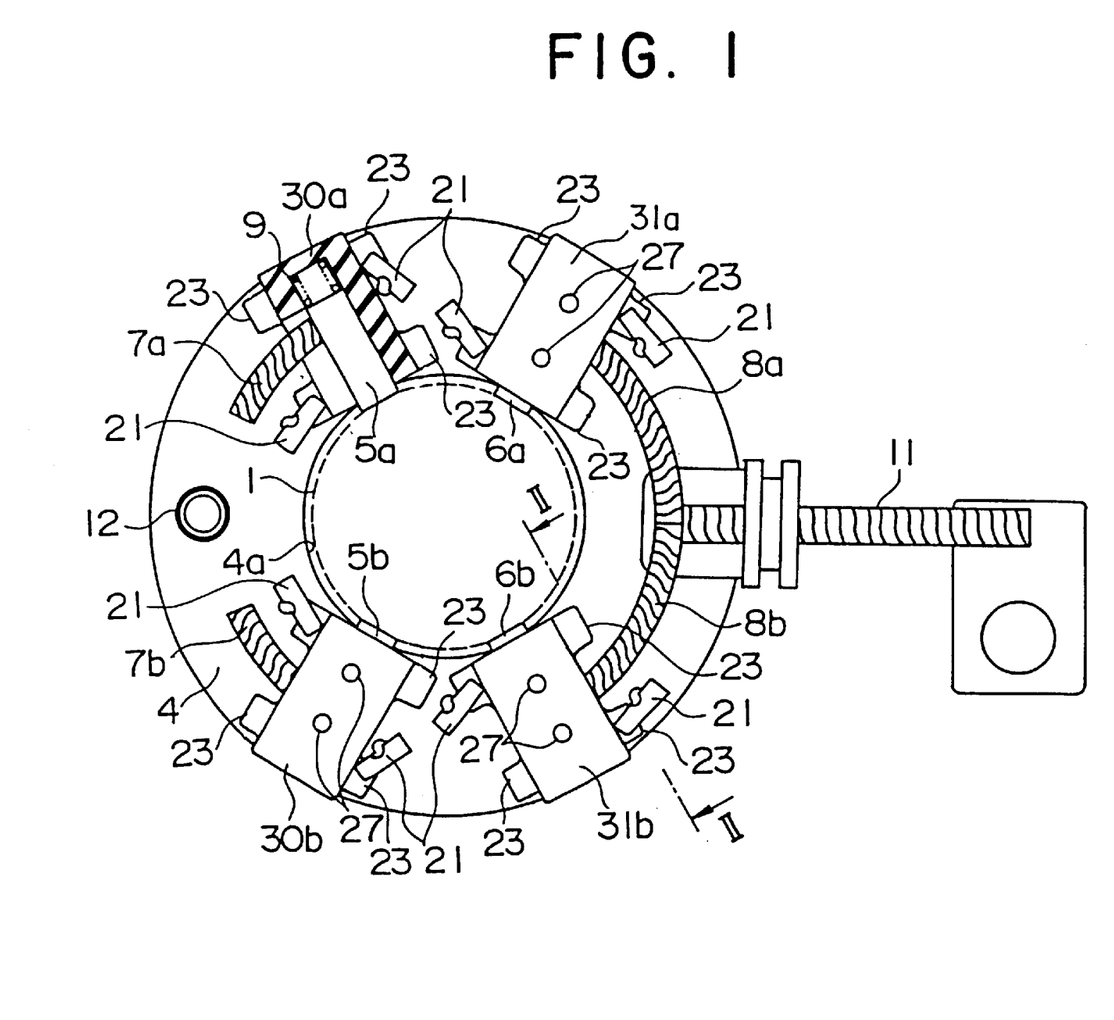
FIG. 1 is a plan of a brush holder assembly according to Embodiment 1 of the present invention.
Figure 2:
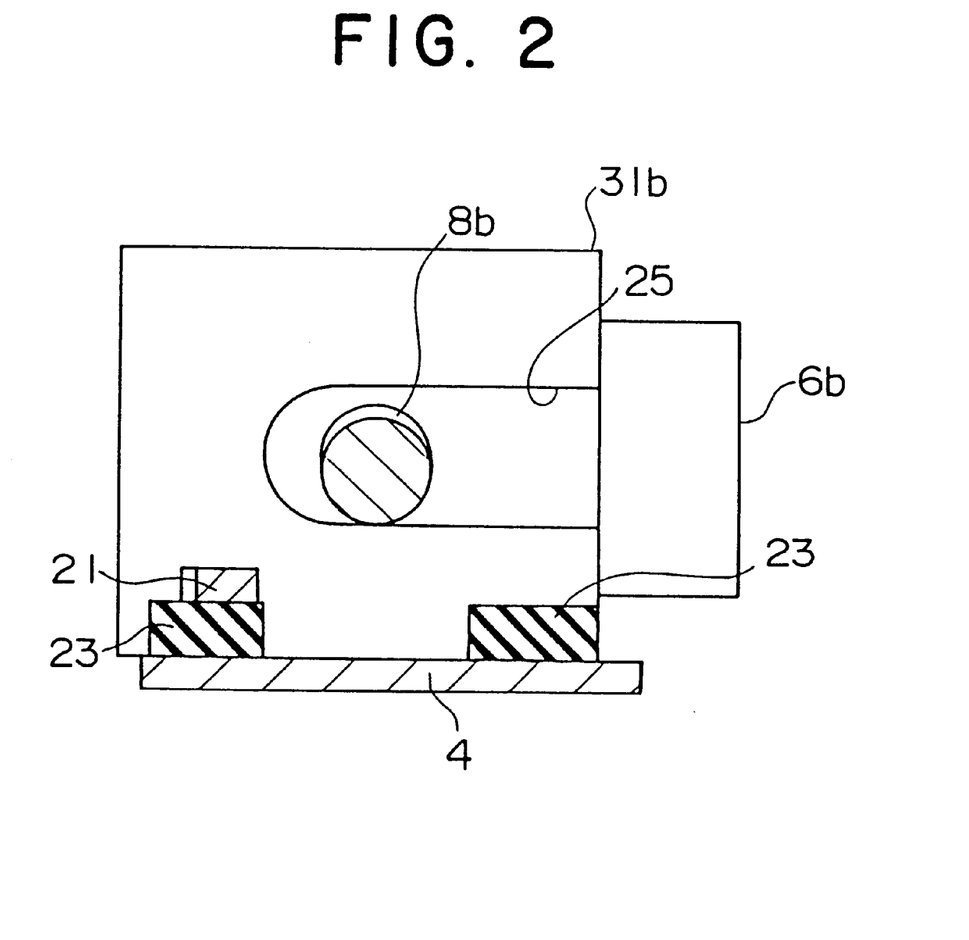
FIG. 2 is a cross-section taken along line II—II in FIG. 1 viewed from the direction of the arrow.
Figure 3:
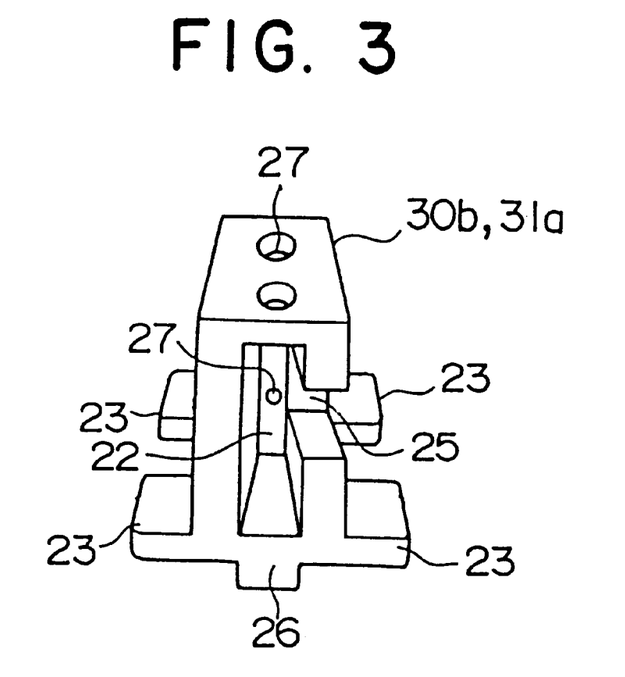
FIG. 3 is a perspective of one of brush holder frames applied to the brush holder assembly according to Embodiment 1 of the present invention.
Figure 4:
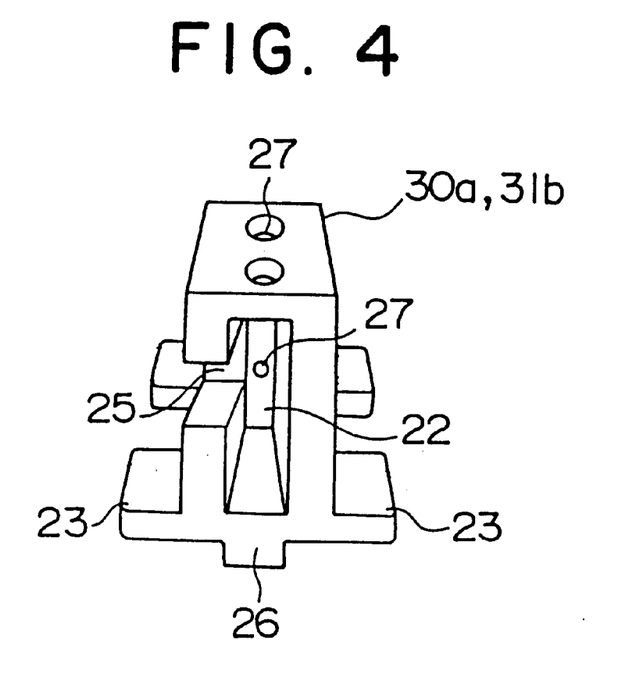
FIG. 4 is a perspective of the other brush holder frame applied to the brush holder assembly according to Embodiment 1 of the present invention.
Figure 5:
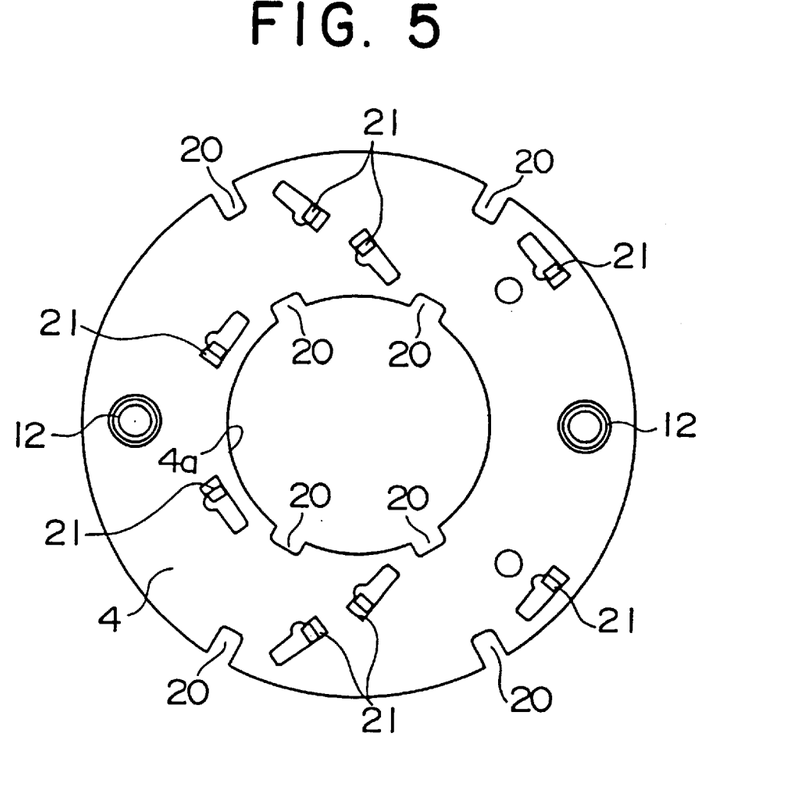
FIG. 5 is a plan of a base applied to the brush holder assembly according to Embodiment 1 of the present invention.

FIG. 1 is a plan of a brush holder assembly according to Embodiment 1 of the present invention, FIG. 2 is a cross-section taken along line II—II in FIG. 1 viewed from the direction of the arrow, FIG. 3 is a perspective of one of brush holder frames applied to the brush holder assembly according to Embodiment 1 of the present invention, FIG. 4 is a perspective of the other brush holder frame applied to the brush holder assembly according to Embodiment 1 of the present invention, and FIG. 5 is a plan of a base applied to the brush holder assembly according to Embodiment 1 of the present invention.

A brush holder assembly comprises a pair of negative-side brush holder frames 30a, 30b and a pair of positive-side brush holder frames 31a, 31b fastened to a base 4.

The base 4 is a steel plate formed into an annulus having a central opening 4a being designed as a passage to allow insertion of a commutator 1. A plurality of notches 20 for positioning brush holder frames are disposed on the inner circumferential edge and the outer circumferential edge of the base 4. Furthermore, a plurality of tabs 21 for securing the brush holder frames are disposed on the base 4 by press working part of the base 4.

Brush receiving recesses 22 are disposed in brush holder frames 30a, 31b, respectively, molded from electrically-insulating synthetic resin so as to extend from a first end towards a second end without penetrating the second end. Furthermore, flanges 23 are disposed so as to extend outwards from both ends of the bottom end on either side. A lead outlet groove 25 is disposed on one side so as to extend from the first end towards the second end and join the brush receiving recess 22 to the outside. Furthermore, protrusions 26 for positioning are disposed on the bottom surface at one end and at the other end. Furthermore, a plurality of radiator openings 27 are provided.

On the other hand, brush holder frames 30b, 31a are constructed similarly to brush holder frames 30a, 31b above, except that the lead outlet groove 25 is disposed on the opposite side of each so as to extend from the first end towards the second end and join the brush receiving recess 22 to the outside.

The brush holder frames 30a, 30b, 31a, 31b are positioned on the base 4 by inserting the protrusions 26 into the positioning notches 20, then fastened to the base 4 by bending the tabs 21 so that the flanges 23 are pressed and secured to the base 4 by the tips of the bent tabs 21. At that point, the brush holder frames 30a, 30b, 31a, 31b are fastened to the base 4 such that the open ends of the brush receiving recesses 22 each face the central opening 4a of the base 4 and the axes of the brush receiving recesses 22 pass through the central axis of the central opening 4a of the base 4. By inserting the protrusions 26 into the positioning notches 20, movement of the brush holder frames 30a, 30b, 31a, 31b in the radial direction and in the direction of rotation is controlled. Furthermore, the tabs 21 securing each of the brush holder frames are bent in mutually opposite circumferential directions, preventing the brush holder frames from dislodging longitudinally.

Furthermore, the negative-side leads 7a, 7b are connected to the rear surface of the negative-side brushes 5a, 5b, and the positive-side leads 8a, 8b are connected to the rear surface of the positive-side brushes 6a, 6b. The negative-side brushes 5a, 5b are each inserted into brush receiving recesses 22 by passing the negative-side leads 7a, 7b through the lead outlet grooves 25 of brush holder frames 30a, 30b. Similarly, the positive-side brushes 6a, 6b are each inserted into brush receiving recesses 22 by passing the positive-side leads 8a, 8b through the lead outlet grooves 25 of brush holder frames 31a, 31b. The brushes 5a, 5b, 6a, 6b are placed in contact with the outer circumferential surface of the commutator 1 inserted through the central opening 4a of the base 4 by the force of brush springs 9 disposed within each of the brush receiving recesses 22.

The negative-side leads 7a, 7b connected to the negative-side brushes 5a, 5b are grounded by connection to the base by welding, etc. On the other hand, the positive-side leads 8a, 8b connected to the positive-side brushes 6a, 6b are connected to a power source (not shown) by means of a connector 11.

This brush holder assembly is mounted on an end bracket of a direct-current electric motor using screw holes 12 disposed in the base 4.

In the brush holder assembly constructed in this manner, the brushes 5a, 5b, 6a, 6b are worn down by the commutator 1 during operation of the direct-current electric motor. As each of the brushes are worn down, they are pressed and moved towards the commutator 1 by the force of the brush springs 9. With the movement of each of the brushes towards the commutator 1, each of the leads move within the outlet grooves 25 towards the commutator 1.

This time, as shown in FIG. 1, the tabs 21 are disposed in positions which secure the flange portions 23 at the second end (the radially outer end) of the positive-side brush holder frames 31a, 31b on the side where the lead outlet groove 25 is disposed and secure the flange portions 23 at the first end (the radially inner end) on the side where the lead outlet groove 25 is not disposed, the tips thereof being bent over so as to press the flange portions 23 against the base 4. As shown in FIG. 2, because each of the tabs 21 disposed on sides where leads pass out are positioned radially outside the range of movement of the positive-side leads 8a, 8b, that is, in positions where the leads 8a, 8b do not come into contact therewith, and as shown in FIG. 1, the tabs 21 are bent over in directions in which the leads 8a, 8b do not come into contact therewith, contact between the tabs 21 and the leads 8a, 8b is structurally avoided.

In this manner, according to Embodiment 1, because each of the tabs 21 disposed on a side of the positive-side brush holder frames 31a, 31b where a lead passes out are positioned radially outside the range of movement of the positive-side leads 8a, 8b, and the tabs 21 are bent over in directions in which the leads 8a, 8b do not come into contact therewith, contact between the tabs 21 and the leads 8a, 8b is structurally avoided, eliminating the need to cover the positive-side leads 8a, 8b with tubing 10. Thus, the operation of applying the tubing 10 is eliminated, making the assembly operation that much easier, and because the tubing 10 is no longer required, costs can be reduced accordingly.

Furthermore, because the brush holder frames 30a, 30b, 31a, 31b are attached to the base 4 by bending the tips of the tabs 21 in opposite directions, dislodgment of the brush holder frames from the base 4 is reliably prevented.

Embodiment 2

Figure 6:
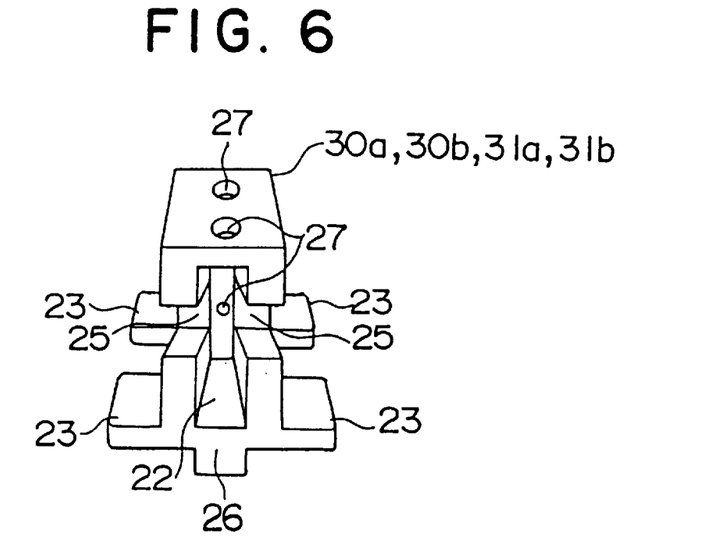
FIG. 6 is a perspective of a brush holder frame applied to a brush holder assembly according to Embodiment 2 of the present invention.

FIG. 6 is a perspective of a brush holder frame applied to a brush holder assembly according to Embodiment 2 of the present invention.

In Embodiment 2, the lead outlet grooves 25 are disposed on both sides of all of the brush holder frames 30a, 30b, 31a, 31b such that each extends from the first end towards the second end and joins the brush receiving recess 22 to the outside.

Incidentally, the other structure is the same as that of the above-described embodiment 1.

In Embodiment 2, because the lead outlet grooves 25 are disposed on both sides of all of the brush holder frames 30a, 30b, 31a, 31b such that each extends from the first end towards the second end and joins the brush receiving recess 22 to the outside, the leads can be passed out either the left- or the right-hand side viewed from the front of the brush holder frames.

Thus, one type of brush holder frame having the same shape can be used for all of the brush holder frames 30a, 30b, 31a, 31b. Furthermore, the molded brush holder frames can all be stored together. In addition, the need to select each brush holder frame to match the direction which the lead is to be passed through is eliminated.

According to the present invention, because each of the tabs disposed on the side of the positive-side brush holder frames holding the positive-side brushes where a lead passes out are positioned radially outside the range of movement of the positive-side leads, and the tips of the tabs are bent in directions in which the positive-side leads do not come into contact therewith, contact between the tabs and the positive-side leads is structurally avoided, eliminating the need for coverage with insulating tubing in order to prevent electrical short circuiting incidents involving the positive-side leads. Thus, the operation of applying tubing, etc., is eliminated, making the assembly operation that much easier, and because tubing, etc., is no longer required, costs can be reduced accordingly.

Furthermore, because the brush holder frames are attached to the base by disposing the tabs in diagonally opposite positions and bending the tips thereof in mutually opposite directions, dislodgment of the brush holder frames from the base can be reliably prevented.

Furthermore, because the lead outlet grooves are disposed on both sides of all of the brush holder frames such that each extends from the first end towards the second end and joins the respective brush receiving recess to the outside, one type of brush holder frame can be used regardless of which direction the lead is to be passed out. Thus, one type of mold for forming the brush holder frames is sufficient, enabling reductions in cost. Furthermore, the molded brush holder frames can all be stored together, allowing reductions in the number of parts and facilitating parts control. Furthermore, there is no need to select a brush holder frame according to the position the brush holder frame will be mounted on the base, improving the assembly operation and preventing poor operations due to incorrect mounting.

What is claimed is:

1. A brush holder assembly, comprising:
a base made of steel plate having a passage for the insertion of a commutator and having a plurality of tabs disposed on a main surface thereof;
a plurality of brush holder frames, each made of insulating synthetic resin and including (1) a brush receiving recess having an opening at a first end and a closure at a second end, (2) a lead outlet groove extending from the first end towards the second end, and (3) flange portions extending outwards from a bottom end on either side, said brush holder frames being disposed on said base such that the openings of said brush receiving recesses face said passage and axes of said brush receiving recesses are directed towards a central axis of said passage, said brush holder frames being secured to said base by bending tips of said tabs;
at least one positive-side brush inserted into said brush receiving recess, such that a positive-side lead attached to said positive-side brush passes through said lead outlet groove in said brush holder frame;
at least one negative-side brush inserted into said brush receiving recess, such that a negative-side lead attached to said negative-side brush passes through said lead outlet groove in said brush holder frame; and
a plurality of brush springs disposed within each of said brush receiving recesses of said brush holder frames for applying force to said positive-side and said negative-side brushes in the direction of the central axis of said passage,
wherein all of said tabs that (1) secure said brush holder frames holding said positive-side brushes and (2) are provided on a side of said brush holder frames wherein said positive-side leads pass through said brush holder frames are positioned radially outside a range of movement of said positive-side leads.

2. The brush holder assembly according to claim 1, wherein said plurality of brush holder frames are attached to said base by disposing said tabs in diagonally opposite positions and bending said tips thereof in mutually opposite directions.

3. The brush holder assembly according to claim 1, wherein said lead outlet grooves are disposed on two sides of all of the brush holder frames such that each extends from the first end towards the second end.

* * * * *